(12) United States Patent
Merendino, Sr.

(10) Patent No.: US 7,568,397 B2
(45) Date of Patent: Aug. 4, 2009

(54) MAGNETIC STABILITY FOR TEST FIXTURE

(75) Inventor: Paul A. Merendino, Sr., Mogadore, OH (US)

(73) Assignee: Bridgestone Firestone North American Tire, LLC, Nashville, TN (US)

( * ) Notice: Subject to any disclaimer, the term of this patent is extended or adjusted under 35 U.S.C. 154(b) by 203 days.

(21) Appl. No.: 11/681,216

(22) Filed: Mar. 2, 2007

(65) Prior Publication Data

US 2008/0210014 A1 Sep. 4, 2008

(51) Int. Cl.
*G01N 3/08* (2006.01)
*G01N 3/02* (2006.01)

(52) U.S. Cl. .............................. 73/856; 73/818; 73/826

(58) Field of Classification Search .................. 73/779, 73/856, 818, 826
See application file for complete search history.

(56) References Cited

U.S. PATENT DOCUMENTS

| | | | |
|---|---|---|---|
| 2,075,968 A * | 4/1937 | von Heydekampf | .......... 73/798 |
| 3,492,566 A | 1/1970 | Gross | |
| 3,575,045 A | 4/1971 | Knights | |
| 3,609,526 A | 9/1971 | Chaberski | |
| 3,675,475 A | 7/1972 | Weinstein | |
| 3,696,664 A | 10/1972 | Moser et al. | |
| 3,746,937 A | 7/1973 | Kolke | |
| 3,854,328 A | 12/1974 | Schmidt | |
| 4,391,087 A * | 7/1983 | Greive et al. | ............... 57/58.52 |
| 4,478,086 A | 10/1984 | Gram | |
| 4,603,588 A | 8/1986 | Niermann et al. | |
| 4,836,029 A * | 6/1989 | Skala et al. | .................... 73/799 |
| 4,869,112 A | 9/1989 | Gram et al. | |
| 4,896,339 A | 1/1990 | Fukumoto | |
| 4,998,441 A | 3/1991 | Stuart | |
| 5,005,424 A | 4/1991 | Markowski | |
| 5,095,757 A | 3/1992 | Larsen et al. | |
| 5,361,640 A | 11/1994 | Carroll et al. | |
| 5,425,276 A | 6/1995 | Gram et al. | |
| 5,448,168 A | 9/1995 | Hirano et al. | |
| 5,535,853 A | 7/1996 | Skalski | |
| 5,693,890 A | 12/1997 | Holmes | |
| 5,719,339 A | 2/1998 | Hartman et al. | |
| 5,767,402 A | 6/1998 | Sandlass et al. | |
| 5,945,607 A | 8/1999 | Peppel et al. | |
| 6,058,784 A | 5/2000 | Carroll et al. | |
| 6,089,101 A | 7/2000 | Ishii et al. | |
| 6,289,744 B1 | 9/2001 | Larson et al. | |

(Continued)

OTHER PUBLICATIONS

Abstract—publication date Sep. 13-16, 1992, pp. 454-459, vol. 1 Control Applications, 1992, First IEEE Conference, Groom, N.J., Britcher, C.P., NASA Res Ctr, Va.

(Continued)

*Primary Examiner*—Lisa M Caputo
*Assistant Examiner*—Jonathan Dunlap
(74) *Attorney, Agent, or Firm*—Thomas R. Kingsbury

(57) ABSTRACT

A test machine for testing the tension or compression properties of a test specimen is provided. The test machine utilizes magnetic force to prevent the fixture of the machine from rotating while placing the test specimen in tension or under compression, which accordingly prevents the test specimen from rotating as well as the source of such rotation. Unintended forces are thereby minimized, enabling a user to obtain more accurate test results.

17 Claims, 4 Drawing Sheets

U.S. PATENT DOCUMENTS

| | | |
|---|---|---|
| 6,389,876 B1 | 5/2002 | Tanimura et al. |
| 6,405,599 B1 | 6/2002 | Patt |
| 6,508,132 B1 | 1/2003 | Lohr et al. |
| 6,526,837 B1 | 3/2003 | Grote et al. |
| 6,591,690 B1 | 7/2003 | Crockford |
| 6,641,067 B2 | 11/2003 | Nakazato |
| 6,679,124 B2 | 1/2004 | Oliver |
| 6,732,591 B2 | 5/2004 | Miles et al. |
| 6,844,721 B2 | 1/2005 | Oliver |
| 6,868,738 B2 | 3/2005 | Moscrip et al. |
| 6,938,494 B2 | 9/2005 | Takada et al. |
| 6,993,410 B2 | 1/2006 | Esterling |
| 7,002,339 B2 | 2/2006 | Kawashima et al. |
| 7,123,450 B1 * | 10/2006 | Villiard et al. .......... 360/261.1 |
| 2002/0017146 A1 | 2/2002 | Oliver |
| 2004/0020306 A1 | 2/2004 | Moscrip et al. |
| 2004/0079166 A1 | 4/2004 | Moscrip et al. |
| 2007/0151337 A1 * | 7/2007 | Cochran ..................... 73/311 |
| 2008/0253031 A1 * | 10/2008 | Yeakley et al. .............. 360/291 |

OTHER PUBLICATIONS

Article, Material Testing Systems Optimized by the Use of Moving Magnet Linear Motors, Kirk Biegler, Endura TEC Systems, Corp, Nov. 2006.

* cited by examiner

MAGNETIC STABILITY FOR TEST FIXTURE

BACKGROUND

The present invention relates to a material testing system capable of applying loads to a test specimen. More particularly, the invention relates to a testing system that utilizes a magnetic force to substantially prevent the specimen from rotating while the load is applied to it.

Various physical properties of materials may be tested. In the field of elastomeric materials, such physical properties may include, shear strain, tensile strength, elongation, compressive strain, among others. In the testing of each particular property, it is beneficial to isolate the forces applied to the test specimen so that only the desired force or forces are being applied to the test specimen. For example, if the shear properties of a specimen were being tested, it would be undesirable to apply an unknown elongation force to the specimen during the shear testing.

The same is true of tensile and compressive testing of a test specimen. It has come to the attention that during the tensile or compression testing of a test specimen, at times the specimen may unintentionally rotate or twist. This rotation of the test specimen introduces an undesirable variable into the test results. Therefore, there is a need to develop a testing apparatus and a test method which will isolate the test specimen, such that unintended forces do not interfere with the physical property testing being conducted.

BRIEF DESCRIPTION

A test machine is provided. The test machine includes an actuator and a fixture in communication with the actuator, wherein the fixture contacts a test specimen. The machine further includes one or more magnets. The magnets are aligned to substantially prohibit the fixture from rotating during the testing. In one embodiment, the testing may include the application of tensile or compressive forces being applied to the test specimen.

A method of testing the tension or compression properties of a test specimen is also provided. The method comprises securing a test specimen between two fixtures, wherein one fixture is in communication with the actuator. The method further includes moving the fixture in the direction of the longitudinal axis of the machine in order to place the specimen in tension or under compression and substantially preventing the fixture from rotating while moving the fixture in the direction of the longitudinal axis of the machine by the use of magnetic force.

DETAILED DESCRIPTION

Figure 1:
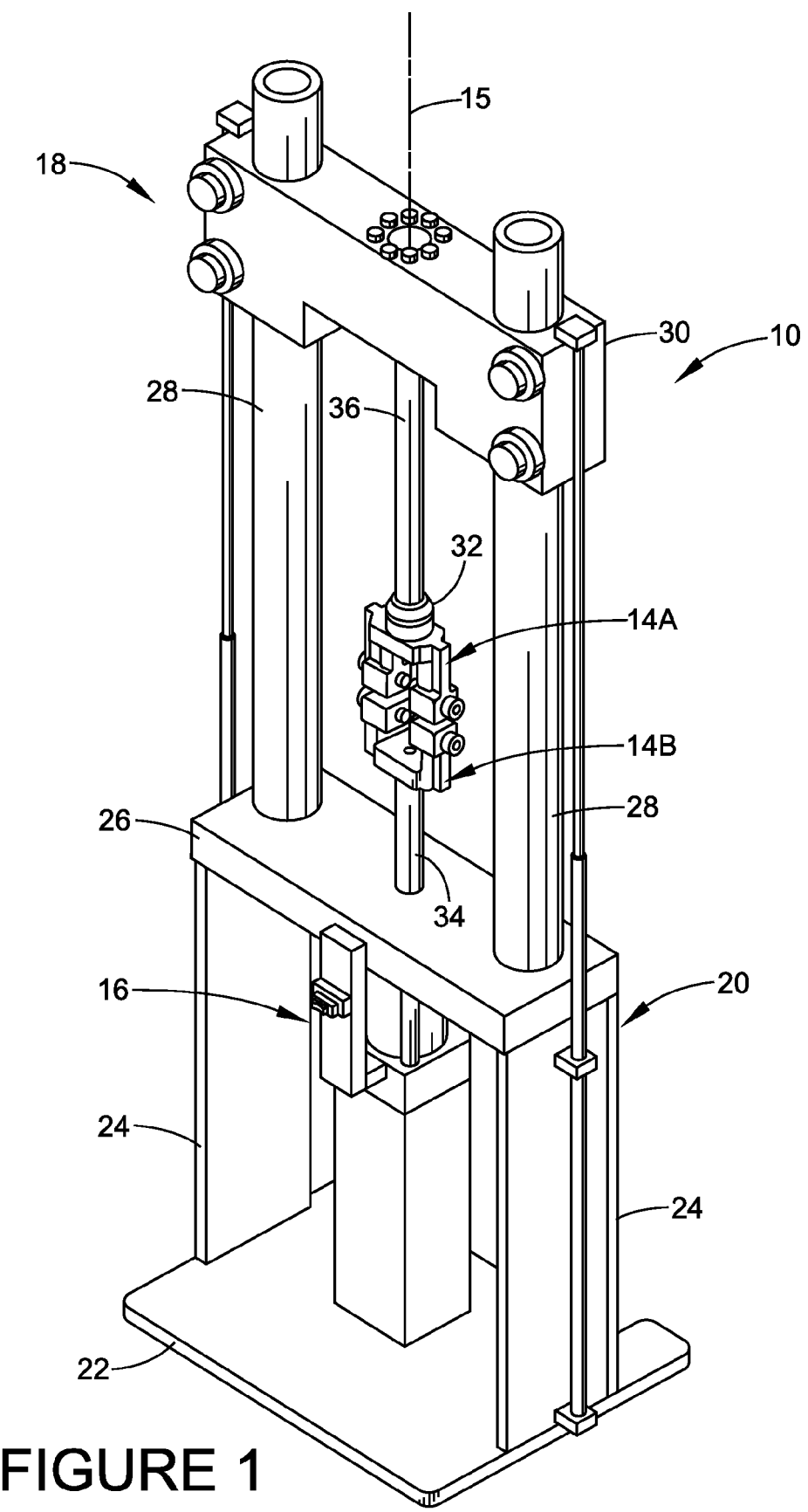
FIG. 1 is a perspective view of a material testing machine.

In the various figures described herein, like reference numerals or the same reference numerals are used to describe like or similar components of the embodiments described herein.

During the tensile or compressive testing of an elastomeric article, it has become apparent that once the article is placed in tension or compressed, the article may exhibit a tendency to undesirably rotate. It has come to the attention of the inventor that the source of the rotation of the article is the rotation of an actuator that is in communication with a fixture gripping the article. Thus, the inventors have developed an apparatus and a technique to inhibit such rotation. Advantageously the technique does not interfere with the ability of the apparatus to apply a compressive force on the test specimen or to place the test specimen in tension. It is preferred that the technique does not mechanically engage the fixture or the test specimen. Mechanically engaged is used herein to describe at least the situation when the two items would come in physical contact.

Examples of mechanical testing equipment which the invention may be applicable are described in the following U.S. Patents, which are hereby incorporated by reference in their entirety U.S. Pat. Nos. 4,478,086, 4,869,112, 5,005,424, 5,361,640, 5,425,276, 5,693,890, 5,719,339, 6,526,837, and 6,679,124. A commercially available example of such an apparatus is the MTS 831 available from MTS Systems Corporation of Eden, Minn.

FIG. 1 illustrates an exemplary material testing apparatus 10 for applying loads to a test specimen. The apparatus 10 includes an upper fixture 14A and a lower fixture 14B that hold the test specimen along a longitudinal axis 15. The lower fixture 14B is connected to an actuator 16 through which loads are applied to the test specimen and reacted against a reaction structure generally indicated at 18. Optionally, the apparatus 10 may include more than one actuator. For example, a second actuator may be located proximate of fixture 14B.

As appreciated by those skilled in the art, the upper fixture 14A and lower fixture 14B, of apparatus 10, can take many forms. Any suitable fixture may be used to practice the invention. Examples of other such fixtures are illustrated in the aforementioned U.S. patents. Preferably, each fixture is able to grip a portion of the test specimen with sufficient retentive force that the fixture is able to retain the test specimen during the desired testing. In one alternate example, fixtures 14A and 14B are capable of retaining the test specimen for compressive testing and fixtures 14A and 14B comprise plates.

In the embodiment illustrated, the material testing apparatus 10 includes a frame 20 having a base 22. A pair of support members 24 extend upwardly from the base 22 and are joined together by a crossbeam 26, which provides a stable support surface. A pair of stationary support columns 28 extends upwardly from the crossbeam 26 to an adjustable crosshead 30. A support 36 extends from crosshead 30 to a load cell 32. Load cell 32 joins the upper fixture 14A to reaction structure 18. The load cell 32 provides a representative signal indicative of tension/compressive forces applied to the test specimen. Alternatively, the load cell may be located in communication with fixture 14B (not shown) instead of fixture 14A, as shown. A further alternative is that apparatus 10 may include more than one load cell. In one of the various embodiments of the apparatus, it is preferred that the actuator or actuators are aligned with an upper or lower fixture and that the load cell or load cells are aligned with the fixture which the actuator is not aligned.

Apparatus 10 further includes an actuator 16. Actuator 16 may be powered by any type of drive system such as an electrical system, a pneumatic system, or a hydraulic system. Support 34 extends from actuator 16 to lower fixture 14B. Preferably actuator 16 is in communication with fixture 14B and actuator 16 may be used to move fixture 14B to apply a tensile force or compressive force to a test specimen.

Optionally apparatus 10 may include a control system that provides control signals along a signal line to actuator 16 (or actuators if the system includes more than one actuator) and receives signals along a control line from load cell 32 which are proportional to the forces measured by the load cell (or load cells if the system includes more than one load cell). Examples of a commercially available control system are the various FLEXTEST® control systems available from MTS Systems Corporation. FLEXTEST is a registered trademark of MTS Systems Corporation.

With respect to the apparatus 10, it was discovered that during the application of either a tensile or compressive force, that actuator 16 exhibited a tendency to rotate which in turn would twist fixture 14B and the test specimen. Typically, upper fixture 14A would not rotate. Therefore, the rotation of actuator 16 would result in an unknown torquing force applied to the test specimen. An aspect of the invention is to prohibit fixture 14B from rotating, more preferably prohibiting both fixture 14B and actuator 16 from rotating. Preferably the rotation of fixture 14B is prohibited without a physical structure coming in contact with fixture 14B. In a preferred embodiment, magnetic force may be used to prohibit the rotation of fixture 14B, as well as, actuator 16.

Figure 2:
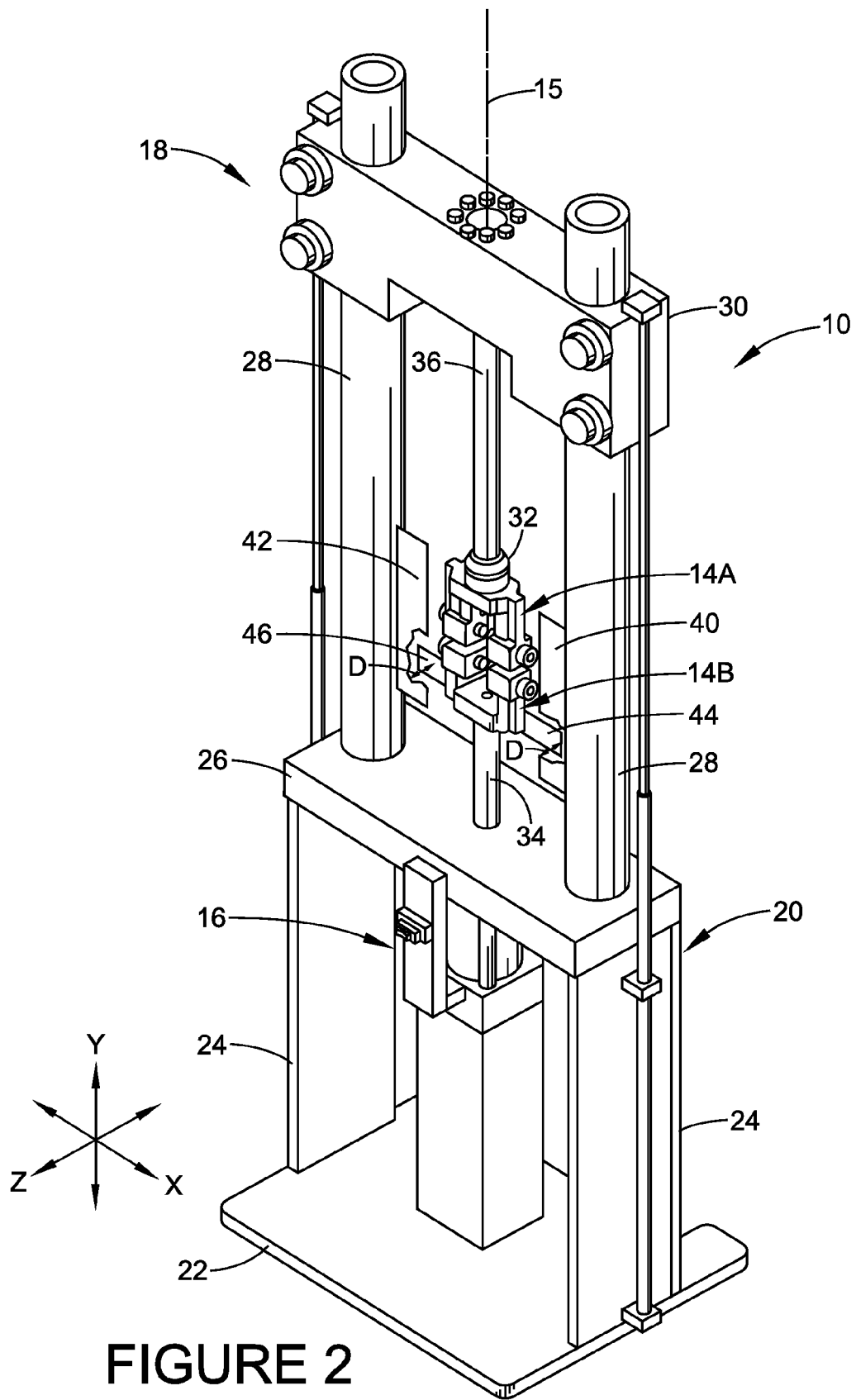
FIG. 2 is a perspective view of a material testing machine which includes an embodiment of the present invention.

With reference to FIG. 2, the apparatus 10 includes a magnet 40 or 42 on each support column 28 respectively. Also a magnet 44 or 46 attached to each side of fixture 14B respectively. Preferably magnets 40 and 42 extend along support columns 28 at a length that at least corresponds with the desired displacement of the test specimen. Also, it is preferred that the magnetic force exerted by magnets 42 and 46 are opposing and the same is preferred for magnets 40 and 44. Preferably magnets 42 and 46, as well as 40 and 44, are spaced apart such that an equilibrium is formed between magnets 42 and 46 and magnets 40 and 44, such that the distance between the opposing magnets D remains substantially constant as magnets 44 and 46 vertically pass by magnets 40 and 42 respectively. Distance D may be defined as the distance between the opposing magnets in the Z-direction.

Preferably the strength of magnets 40, 42, 44, and 46 are sufficient to prohibit fixture 14B from rotating in either direction, more preferably sufficient to prohibit both fixture 14B and actuator 16 from rotating in either direction. With respect to magnets 40, 42, 44, and 46, a preferred range of strength for each magnet may be about 5 to 15 lbs. The invention is not limited to any particular type of magnet, as any particular material which has the ability of attracting a like material may be used. For example various types of magnets such as electro-magnets, rare earth magnets, and combinations thereof may be used to practice the invention.

Figure 3:
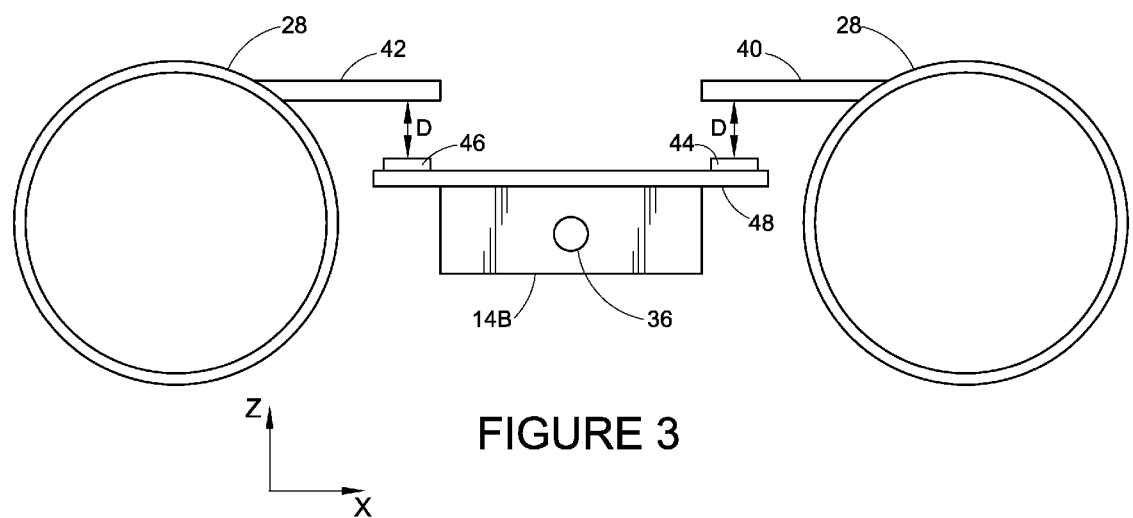
FIG. 3 is a top view of the relationship of the magnets in one embodiment of the invention.

With reference to FIG. 3, magnets 40 and 42 are placed along support columns 28. Magnets 44 and 46 are attached to each side of fixture 14B. In the embodiment shown, magnets 44 and 46 are placed on structure 48, which in turn is attached to fixture 14B. The magnetic force exerted by magnets 42 and 46 are opposing to each other, and the same is preferred for magnets 40 and 44. Preferably magnets 42 and 46, as well as 40 and 44, are spaced apart such that an equilibrium is formed between magnets 42 and 46 and magnets 40 and 44, such that the distance between the opposing magnets D remains substantially constant as magnets 44 and 46 vertically pass by magnets 40 and 42 respectively. Distance D may be defined as the distance between the opposing magnets in the Z-direction.

Figure 4:
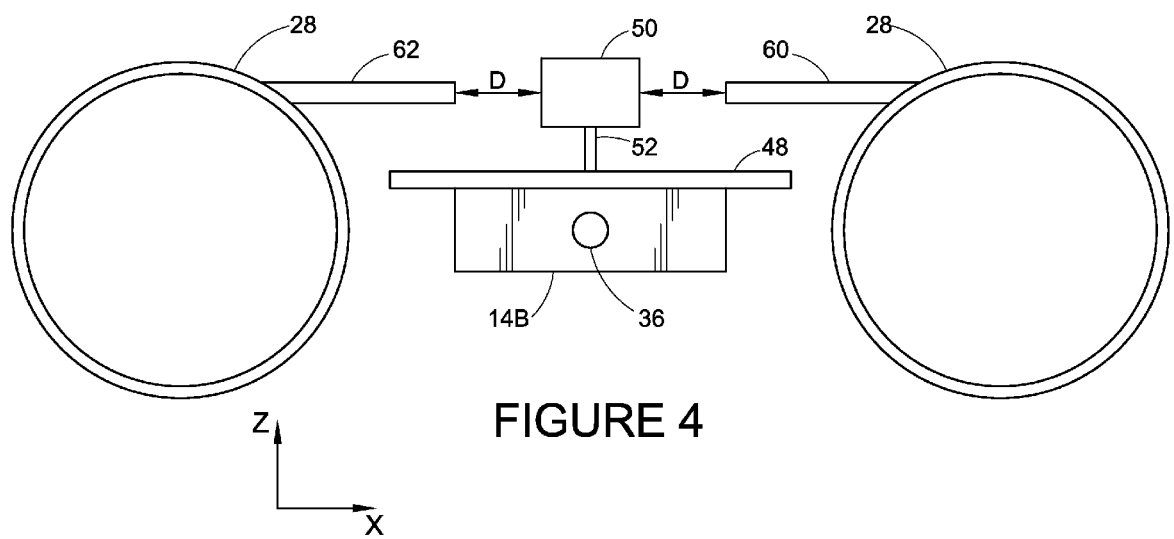
FIG. 4 is a top view of a material testing machine which includes another embodiment of the present invention.

Another embodiment of the invention is illustrated in FIG. 4. In this particular embodiment, apparatus 10 may include one or more magnets. Preferably, in this embodiment, one magnet 50 is attached to arm 52 which extends from structure 48. Preferably, magnet 50 is located at an equilibrium position between structures 60 and 62 so that a substantially equal magnet force is applied toward each structure and the force prohibits the aforementioned rotation of fixture 14B. The single magnet embodiment is not limited to the particular embodiment shown in FIG. 4. In an alternate embodiment, the magnet may extend from an arm attached to support 34 instead of a structure connected to lower fixture 14B.

A further embodiment contemplated may include a hybrid of the embodiments, illustrated in FIGS. 2 and 4. In this particular embodiment, magnet 50 may be attached to fixture 14B or attached to a structure which is attached to fixture 14B as described above. Magnets 40 and 42 may be attached to columns 28 as illustrated in FIG. 2. Preferably magnet 50 would exert a magnetic force outward in the x direction toward magnets 40 and 42 and magnets 40 and 42 would exert an opposing magnetic force back in the direction of magnet 50, thereby locating magnet 50 at an equilibrium location between magnets 40 and 42.

A method of testing the tension properties of a test specimen is also provided. The test specimen is secured between fixtures 14A and 14B. The test specimen is moved a selected distance by actuator 16 in a direction that coincides with the longitudinal axis 15 of the machine to place the specimen in tension. A load cell 32 measures the forces applied to the test specimen. Preferably, a system capable of monitoring the force measurements from load cell 32 is provided (not shown).

Magnetic force is used to prevent fixture 14B, and more preferably fixture 14B and actuator 16, from rotating while fixture 14B moves in the direction which coincides with longitudinal axis 15. Preferably, magnets 40 and 42 are placed on each support column 28, respectively. More preferably, magnets 40 and 42 extend along support columns 28 at least the distance of the displacement of fixture 14B. Magnets 44 and 46 are attached to each side of fixture 14B, respectively. Alternatively, magnets 44 and 46 may be attached to fixture 14B by attaching magnets 44 and 46 to a structure and attaching the structure to fixture 14B. In an alternative embodiment, magnets 44 and 46 may be attached to support 34 by attaching magnets 44 and 46 to a structure and attaching the structure to support 34. Preferably, the magnetic force exerted by magnets 42 and 46 are opposing to each other, and the same is preferred for magnets 40 and 44. It is also preferable that magnets 42 and 46, as well as 40 and 44, are spaced apart such that an equilibrium is formed between magnets 42 and 46 and magnets 40 and 44, such that the distance between the opposing magnets D remains substantially constant as magnets 44 and 46 vertically pass by magnets 40 and 42 respectively. This may be done by placing magnets 46 and 44 substantially equidistance apart from fixture 14B or support 34 in the plane perpendicular to longitudinal axis 15.

The above method may be modified to practice the aforementioned single magnet or three magnet embodiments also. In the single magnet embodiment, magnet 50 is attached to arm which extends from either of a structure attached to fixture 14B or support 34. Preferably magnet 50 exerts a sufficient magnetic force on both of structures 60 and 62 so to prohibit the rotation of fixture 14B. In three magnet alternate embodiment, the rotation of fixture 14B is prohibited by aligning magnet 50, shown in FIG. 4, between opposing magnets 40 and 42, as illustrated in FIG. 2 and described above.

The test specimen may be any shape to test the tension properties. To allow for easier retention by fixtures 14A and 14B, a rectilinear shaped test specimen is preferred when testing the tension properties.

A method of testing the compression properties of a test specimen is also provided. When testing compression properties, in one embodiment, fixtures 14A and 14B are preferably plates that oppose each other (not shown). The test specimen is placed between fixtures 14A and 14B. Actuator 16 engages fixture 14B to move fixture 14B a predetermined distance to apply a selected compressive force on the test specimen. Load cell 32 may be used to measure the compressive force applied. Preferably, a system capable of monitoring the force measurements from load cell 32 is provided (not shown).

When testing the tension or compression properties, the test specimen may be any material. Examples of such materials include rubbers, textiles, plastics, metals, and combinations thereof.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A test machine comprising:
   an actuator;
   support columns;
   a fixture connected with said actuator and said support columns, wherein said fixture contacts a test specimen;
   a magnet, wherein said magnet is located to substantially prohibit rotation of the fixture while the fixture moves in a direction of a longitudinal axis of the machine; and
   a pair of metal plates extending from said support columns, each plate having at least a segment constructed from a material able to attract the magnet, the magnet aligned at an equilibrium position between the plates.

2. The test machine of claim 1 wherein said magnet comprises a first set of at least two magnets.

3. The test machine of claim 2, further comprising a second set of at least two magnets.

4. The test machine of claim 1, further comprising a load cell.

5. The test machine of claim 4, wherein said drive system includes a hydraulic system, a pneumatic system, or an electrical system.

6. The test machine of claim 1, further comprising a drive system in communication with the actuator.

7. A method of testing the tension or compression properties of a test specimen, the method comprising:
   securing a test specimen between two fixtures, wherein one of said fixtures is connected with a support column;
   moving at least one of said fixtures along the a longitudinal axis of the machine in order to place the specimen in tension or under compression; and
   directing a first magnetic force in a first direction from a first magnet connected to the moving fixture; and
   directing a second magnetic force in a second direction from a second magnet connected to the support column, wherein the first magnetic force opposes the second magnetic force to substantially prevent the moving fixture from rotating.

8. The method of claim 7, determining the force exerted on the test specimen.

9. The method of claim 8, further comprises monitoring the force.

10. The method of claim 7, wherein the second magnet includes a pair of magnets aligned along opposing sides of the first magnet, each of the pair of magnets directing an opposing magnetic force toward the first magnet.

11. The method of claim 10, wherein the second magnet includes a pair of magnets aligned along opposing sides of the first magnet, wherein the first magnet is at an equilibrium position between each pair of magnets.

12. The method of claim 7, wherein the first magnet includes at least two magnets connected to the moving fixture and the second magnet includes at least two magnets.

13. A test machine comprising:
   an actuator;
   a support column;
   a fixture connected with the actuator and the support column, the fixture contacts an associated test specimen and moves with respect to the support column along an axis of the test machine;
   a first magnet attached to the fixture;
   a second magnet attached to the support column, wherein a magnetic force exerted by the first magnet is opposed to a magnetic force exerted by the second magnet to inhibit rotation of the fixture.

14. The test machine of claim 13 further comprising a load cell.

15. The test machine of claim 13, wherein the second magnet includes a pair of magnets aligned along opposing sides of the first magnet, each of the pair of magnets directing an opposing magnetic force toward the first magnet.

16. The test machine of claim 13, wherein the second magnet includes a pair of magnets aligned along opposing sides of the first magnet, wherein the first magnet is at an equilibrium position between each pair of magnets.

17. The test machine of claim 13, wherein the second magnet extends along the support column a length that corresponds with a displacement of the associated test specimen.

* * * * *